US012643901B2

(12) United States Patent
Connon et al.

(10) Patent No.: US 12,643,901 B2
(45) Date of Patent: Jun. 2, 2026

(54) COMPOUNDS

(71) Applicant: The Provost, Fellows, Foundation Scholars, and the other members of Board, of the College of the Holy and Undivided Trinity of Queen Elizabeth, near Dublin, Dublin (IE)

(72) Inventors: Stephen Connon, Dublin (IE); Ursula Fearon, Dublin (IE); Vincent Kelly, Dublin (IE); John Southern, Dublin (IE)

(73) Assignee: The Provost, Fellows, Foundation Scholars, and the other members of Board, of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 561 days.

(21) Appl. No.: 18/018,359

(22) PCT Filed: Jul. 28, 2021

(86) PCT No.: PCT/EP2021/071185

§ 371 (c)(1),
(2) Date: Jan. 27, 2023

(87) PCT Pub. No.: WO2022/023433

PCT Pub. Date: Feb. 3, 2022

(65) Prior Publication Data

US 2023/0286987 A1 Sep. 14, 2023

(30) Foreign Application Priority Data

Jul. 29, 2020 (GB) ...................................... 2011812

(51) Int. Cl.
*C07D 487/04* (2006.01)
*A61P 25/28* (2006.01)
*A61P 37/00* (2006.01)

(52) U.S. Cl.
CPC ............ *C07D 487/04* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 6,106,864 | A | 8/2000 | Dolan et al. |
| 2018/0148764 | A1 | 5/2018 | Devaraj et al. |

FOREIGN PATENT DOCUMENTS

| | | | |
|---|---|---|---|
| WO | 9111172 | A1 | 8/1991 |
| WO | 9402518 | A1 | 2/1994 |
| WO | 9855148 | A1 | 12/1998 |
| WO | 0035298 | A1 | 6/2000 |
| WO | 2005016235 | A3 | 3/2006 |
| WO | 2016050804 | A1 | 4/2016 |
| WO | 2016050806 | A1 | 4/2016 |

OTHER PUBLICATIONS

Boland et al., "Queuosine Formation in Eukaryotic tRNA Occurs via a Mitochondria-localized Heteromeric Transglycosylase," The Journal of Biological Chemistry, vol. 284, No. 27, pp. 18218-18227, Jul. 3, 2009.

Fergus et al., "The Queuine Micronutrient: Charting a Course from Microbe to Man," Nutrients, 2015, 7(4):2897-2929.

Hayes et al., "Queuine Micronutrient Deficiency Promotes Warburg Metabolism and Reversal of the Mitochondrial ATP Synthase in Hela Cells," Nutrients 2020, 12, 871.

Verma et al., "Current Status of Drug Delivery Technologies and Future Directions," Pharmaceutical Technology On-line, 25 (2), 1-14, 2001.

Liang et al., "Fast-dissolving intraoral drug delivery systems," Expert Opinion in Therapeutic Patents, 2001, 11 (6), 981-986.

Stromnes et al., "Active induction of experimental allergic encephalomyelitis," Nature Protocols, 2006, 1(4), 1810-19.

Alqasem et al., "The eukaryotic tRNA-guanine transglycosylase enzyme inserts queuine into tRNA via a sequential bi-bi mechanism†," Chem. Commun., 2020, 56, 3915-3918.

PCT International Search Report and Written Opinion for International Application No. PCT/EP2021/071185, dated Oct. 14, 2021, 10 pages.

Great Britain Search Report for Application No. GB2011812.1, dated Jan. 11, 2021, 2 pages.

Fergus et al., "The Queuine Micronutrient: Charting a Course from Microbe to Man," Nutrients, vol. 7, No. 4, Apr. 15, 2015, pp. 2897-2929.

*Primary Examiner* — Sun Jae Yoo

(74) *Attorney, Agent, or Firm* — Hoffman Warnick LLC

(57) ABSTRACT

The present invention provides a compound of formula (I), or pharmaceutically acceptable salt or solvate thereof, wherein: Y is selected from C or N; X is O; bond a is a single or double bond; x is 1 when a is a single bond and x is 0 when a is a double bond; $R_1$ is selected from hydrogen and methyl; $R_2$ (when present) is selected from hydrogen and methyl; $R_3$ is selected from hydrogen, (1-6C)alkyl and (1-6C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

(I)

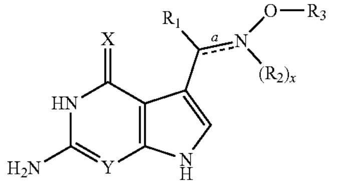

17 Claims, No Drawings

COMPOUNDS

FIELD

The present invention relates to novel compounds and to their use in the treatment of conditions mediated by the queuine-tRNA ribosyltransferase pathway (also known as the 'TGT' pathway), including autoimmune diseases, such as multiple sclerosis and rheumatoid arthritis, and neurodegenerative conditions such as Parkinson's and Alzheimer's disease. The present invention also relates to pharmaceutical compositions comprising the novel compounds.

BACKGROUND TO THE INVENTION

The TGT pathway, also known as the queuine tRNA ribosyltransferase (QTRT) enzyme pathway, was first elucidated in a 2009 publication (Boland et al., *J. Biol. Chem.* 2009. 3; 284(27):18218-27). Cells which proliferate at an abnormal rate, such as T-cells in autoimmune disease, have been found to be queuine deficient (Fergus et al., *Nutrients* 2015, 7(4):2897-2929).

The TGT pathway has been exploited to provide treatment for diseases. WO 2016/050804 and WO 2016/050806 each describe queuine mimetic compounds that act via the TGT pathway suitable for use in the treatment autoimmune diseases, especially multiple sclerosis (MS), rheumatoid arthritis (RA), irritable bowel disease (IBD) and diabetes.

The present invention provides new compounds for use in treating diseases mediated by the TGT pathway.

There is a strong need for new treatments for autoimmune diseases in particular. Most autoimmune diseases are not currently uncurable, with existing treatments focussing on ameliorating the symptoms. Autoimmune diseases, such as MS, RA, alopecia areata, IBD and diabetes, are debilitating diseases that exhibit a range of symptoms. There are currently no cures for autoimmune diseases, only treatments for the wide-ranging symptoms associated with these diseases which are treated using a range of medications. Many of the medications that are used are only moderately effective and can have adverse effects for the patients, such that they are poorly tolerated. New medications for the treatment of autoimmune diseases are therefore highly desired.

For example, MS is an autoimmune disease that causes a wide range of symptoms including fatigue, blurred vision, cognitive impairment, and spasticity. Many sufferers develop irreversible motor disability and 50% of sufferers are unable to walk unassisted within 15 years of the onset of the disease. At present, there is no known cure for MS, although medications do exist to treat symptoms of the disease. Examples of such medicaments include fingolimod, teriflunomide, dimethyl fumarate (Tecifdera), ocrelizumab, siponimod, cladribine and random polymer glatiramer acetate. These medicines act to alter the rate of relapse and remission of disease onset and/or severity, but they do not reverse disease progression and are associated with numerous harmful side effects. For some sub classes of MS, such as progressive MS only a small fraction of patients derive any benefit from existing medications.

RA is another autoimmune disease that cases a wide range of symptoms, including joint pain and stiffness, fatigue, high temperature, sweating and poor appetite. Similarly to MS, there is currently no known cure for RA, and patients are treated with medications to ease disease symptoms such as the inflammation of the joints to minimise damage. Typically, patients are administered disease modifying treatments such as methotrexate, leflunomide, hydroxychloroquine and sulfasalazine.

Common side-effects of methotrexate include feeling sick, loss of appetite, a sore mouth, diarrhoea, headaches and hair loss. Patients treated with methotrexate are also required to have regular blood tests to check for damage to liver and blood cells, and may require X-rays to check for lung damage.

Biological treatments, such as etanercept and infliximab, are a newer form of treatment for RA. Patients can suffer serious infection related side-effects with these treatments.

JAK inhibitors are a new class of RA drugs and include tofacitinib and baricitinib.

Another area of significant medical need is neurodegeneration, with treatments particularly sought for indications such as Alzheimers and Parkinsons disease.

Thus, there is a desire to provide an effective, tolerable treatment for an autoimmune disease such as MS and RA and neurodegenerative diseases.

SUMMARY OF THE INVENTION

It is one aim of the present invention, amongst others, to provide a compound that is useful for the treatment of conditions mediated by the TGT pathway, such as for the treatment of an autoimmune disease, such as MS and/or RA.

The present invention provides a compound of formula (I):

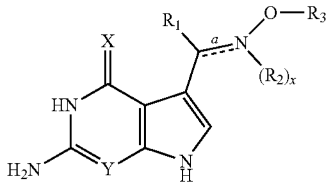

(I)

or pharmaceutically acceptable salt or solvate thereof, wherein:

Y is selected from C or N;

X is O;

bond a is a single or double bond;

x is 1 when a is a single bond and x is 0 when a is a double bond;

$R_1$ is selected from hydrogen and methyl;

$R_2$ (when present) is selected from hydrogen and methyl;

$R_3$ is selected from hydrogen, (1-6C)alkyl and (1-6C) alkyl-phenyl, wherein said phenyl is optionally substituted by one or more (for example by 1 to 3) substituents each independently selected from hydroxy, (1-6C) alkoxy, (1-6C)alkyl and halo (such as chloro and and fluoro).

The present invention also provides a compound of the invention, or a pharmaceutically acceptable salt or solvate thereof, for use as a medicament.

The present invention also provides a compound of the invention, or a pharmaceutically acceptable salt or solvate thereof, for use in the treatment of a disease or medical condition mediated by the queuine-tRNA ribosyltransferase pathway.

The present invention also provides a compound of the invention, or a pharmaceutically acceptable salt or solvate thereof, for use in the treatment of an autoimmune disease.

The present invention also provides a compound of the invention, or a pharmaceutically acceptable salt or solvate thereof, for use in the treatment of a neurodegenerative disease.

The present invention also provides a compound of the invention, or a pharmaceutically acceptable salt or solvate thereof, for use in the treatment of an inflammatory disease.

The present invention also provides a pharmaceutical composition comprising a compound of the invention, or a pharmaceutically acceptable salt or solvate thereof, and a pharmaceutically acceptable carrier or excipient.

The present invention also provides a pharmaceutical product comprising a compound of the invention, or a pharmaceutically acceptable salt or solvate thereof, and an additional therapeutic agent.

The present invention also provides a containerised pharmaceutical product comprising a container containing a pharmaceutical composition comprising a compound of the invention, or a pharmaceutically acceptable salt or solvate thereof, and instructions directing use of the pharmaceutical composition in the treatment of an autoimmune, neurodegenerative or inflammatory disease.

DETAILED DESCRIPTION OF THE INVENTION

The present invention provides novel compounds, uses of the compounds as medicaments, pharmaceutical compositions and pharmaceutical products as set out in the appended claims. Other features of the invention will be apparent from the dependent claims, and the description that follows.

Unless otherwise stated, the following terms used in the specification and claims have the meanings set out below.

The term “comprising” or “comprises” means including the component(s) specified but not to the exclusion of the presence of other components. The term “consisting essentially of” or “consists essentially of” means including the components specified but excluding other components except for materials present as impurities, unavoidable materials present as a result of processes used to provide the components, and components added for a purpose other than achieving the technical effect of the invention. The term “consisting of” or “consists of” means including the components specified but excluding other components.

Whenever appropriate, depending upon the context, the use of the term “comprises” or “comprising” may also be taken to include the meaning “consists essentially of” or “consisting essentially of”, and may also be taken to include the meaning “consists of” or “consisting of”.

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

References to “treating” or “treatment” include prophylaxis as well as the alleviation of established symptoms of a disease or medical condition. “Treating” or “treatment” of a disease or medical condition therefore includes: (1) preventing or delaying the appearance of clinical symptoms of the disease or medical condition developing in a human that may be afflicted with or predisposed to the disease or medical condition but does not yet experience or display clinical or subclinical symptoms thereof, (2) inhibiting the disease or medical condition, i.e. arresting, reducing or delaying the development of the disease or medical condition, or a relapse thereof (in case of maintenance treatment) or at least one clinical or subclinical symptom thereof, or (3) relieving or attenuating the disease, i.e. causing regression of the disease or medical condition or at least one of its clinical or subclinical symptoms.

A “therapeutically effective amount” means the amount of a compound that, when administered to a mammal for treating a disease, is sufficient to effect such treatment for the disease. The “therapeutically effective amount” will vary depending on the compound, the disease and its severity, the mode of administration and the age, weight, etc., of the mammal to be treated.

The term “(1-6C)alkyl” refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. “(1-3C)alkyl” similarly refers to such groups containing 1, 2 or 3 carbon atoms.

The term “(1-6C)alkoxy” refers to a —O-alkyl group, where alkyl is as defined above. (1-6C)alkoxy includes an alkyl group having from 1 to 6 carbon atoms. Non-limiting examples of (1-6C)alkoxy groups include methoxy, ethoxy, n-propoxy, iso-propoxy, 2-methyl-1-propoxy, 2-methyl-2-propoxy, n-butoxy, sec-butoxy, tert-butoxy, n-pentoxy and n-hexoxy.

The term “halo” refers to one of the halogens, group 17 of the periodic table. In particular, the term refers to fluoro, chloro, bromo and iodo. Preferably, the term refers to fluoro or chloro.

Where a moiety is substituted, it may be substituted at any point on the moiety where chemically possible and consistent with atomic valency requirements. The moiety may be substituted by one or more substituents, e.g. 1, 2 or 3 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible.

The phrase “compound of the invention” means those compounds, i.e. of formula (I), that are disclosed herein, both generically and specifically, as well as pharmaceutically acceptable salts or solvates thereof.

Compounds

The present invention provides a compound of formula (I):

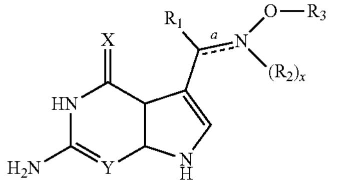

(I)

or pharmaceutically acceptable salt or solvate thereof, wherein:

Y is selected from C or N;

X is O;

bond a is a single or double bond;

x is 1 when a is a single bond and x is 0 when a is a double bond;

$R_1$ is selected from hydrogen and methyl;

$R_2$ (when present) is selected from hydrogen and methyl;

$R_3$ is selected from hydrogen, (1-6C)alkyl and (1-6C) alkyl-phenyl, wherein said phenyl is optionally substituted by one or more (for example 1 to 3) substituents each independently selected from hydroxy, (1-6C) alkoxy, (1-6C)alkyl and halo (such as chloro and fluoro).

When reference is made herein to bond a representing a single bond (and x is 1), then the resultant structure is as follows represented as formula (IA):

(IA)

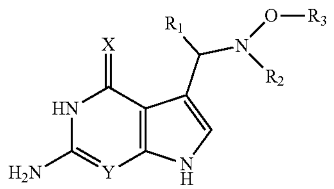

wherein Y, X, $R_1$, $R_2$ and $R_3$ are as defined herein.

When reference is made herein to bond a representing a double bond (and x is 0), then the resultant structure is as follows represented as formula (IB):

(IB)

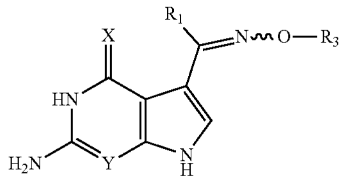

wherein Y, X, $R_1$ and $R_3$ are as defined herein. In the compounds of formula (IB), in which a represents a double bond, the compounds may exist as two geometric isomers, i.e. isomers having an E- and a Z-configuration, due to the presence of the oxime group. The generic formula (I) encompasses both mixtures of geometric isomers and separate, individual geometric isomers.

When the group $R_3$ represents (1-6C)alkyl-phenyl, the group is attached to the oxygen via the alkyl group, so as to form a group —O-[(1-6C)alkyl]phenyl.

The compounds of the invention can contain one or more chiral centres and the generic formula (I) encompasses both the racemate and separate, individual enantiomeric forms.

The compounds of the present invention are substrates for the TGT enzyme and are distinguished over other queuine mimetic compounds by their enhanced efficacy as treatments. Typically, the compounds of the present invention are more potent, have a more favourable pharmacokinetic profile, better bioavailability, tolerability, and/or stability, and/ or are easier to formulate and/or to manufacture than other queuine mimetic compounds.

Suitably, in the formula (I) Y is N.

Suitably, in the formula (I) $R_1$ is hydrogen.

Suitably, in the formula (I) Y is N.

Suitably, in the formula (I) Y is N and $R_1$ is hydrogen.

Suitably, in the formula (I) a is a double bond and x is 0.

Suitably, in the formula (I) a is a single bond and x is 1.

Suitably, when x is 1, $R_2$ is hydrogen.

Suitably, in the formula (I) $R_3$ is selected from hydrogen, (1-6C)alkyl and (1-6C)alkyl-phenyl, wherein said phenyl is unsubstituted.

Suitably, in the formula (I) Y is N and $R_3$ is selected from hydrogen, (1-6C)alkyl and (1-6C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

Suitably, in the formula (I) Y is N and $R_3$ is selected from hydrogen, (1-6C)alkyl and (1-6C)alkyl-phenyl, wherein said phenyl is unsubstituted.

Suitably, in the formula (I) $R_3$ is selected from hydrogen, (1-3C)alkyl and (1-4C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

Suitably, in the formula (I) $R_3$ is selected from hydrogen, (1-3C)alkyl and (1-4C)alkyl-phenyl, wherein said phenyl is unsubstituted.

Suitably, in the formula (I) Y is N and $R_3$ is selected from hydrogen, (1-3C)alkyl and (1-4C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

Suitably, in the formula (I) Y is N and $R_3$ is selected from hydrogen, (1-3C)alkyl and (1-4C)alkyl-phenyl, wherein said phenyl is unsubstituted.

Suitably in the formula (I) $R_3$ is selected from hydrogen, $CH_3$ and (1-2C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

Suitably in the formula (I) $R_3$ is selected from hydrogen, $CH_3$ and (1-2C)alkyl-phenyl, wherein said phenyl is unsubstituted.

Suitably, in the formula (I) Y is N and $R_3$ is selected from hydrogen, $CH_3$ and (1-2C)alkyl-phenyl, wherein said phenyl is optionally substituted by one or more (for example 1 to 3) substituents each independently selected from hydroxy, (1-6C)alkoxy, (1-6C)alkyl and halo (such as chloro and fluoro).

Suitably, in the formula (I) Y is N and $R_3$ is selected from hydrogen, $CH_3$ and (1-2C)alkyl-phenyl, wherein said phenyl is unsubstituted.

The present invention also provides a compound of formula (I), or pharmaceutically acceptable salt or solvate thereof, selected from:

2-amino-5-((phenethoxyamino)methyl)-3,7-dihydro-4H-pyrrolo[2,3-d]pyrimidin-4-one;

2-amino-4-oxo-4,7-dihydro-3H-pyrrolo[2,3-d]pyrimidine-5-carbaldehyde O-methyl oxime;

2-amino-5-(((benzyloxy)amino)methyl)-3,7-dihydro-4H-pyrrolo[2,3-d]pyrimidin-4-one; and 2-amino-4-oxo-4,7-dihydro-3H-pyrrolo[2,3-d]pyrimidine-5-carbaldehyde oxime.

Suitably the compounds are obtained as the HCl salts.

A suitable pharmaceutically acceptable salt of a compound of formula (I) is for example an acid-addition salt, such as an acid-additional salt with hydrochloric acid, citric acid, tartaric acid and fumaric acid (particularly hydrochloric acid). An acid-addition salt may be obtained, for example, by reaction of a compound of formula (I) with a suitable acid (such as hydrochloric acid, citric acid, tartaric acid and fumaric acid) using a conventional procedure.

A pharmaceutically acceptable salt may alternatively be formed by converting one salt of a compound of the invention to another by reaction with an appropriate acid or base, or by means of a suitable ion exchange column.

The preparation of a pharmaceutically acceptable salt is typically conducted in solution. The resulting salt may precipitate out and be collected by filtration or may be recovered by evaporation of the solvent.

The compounds of formula (I) may form salts in situ under physiological conditions, for example when used as a medicament.

It is to be understood that the compounds of formula (I) may exist in solvated or unsolvated forms, such as for example hydrated forms. The invention encompasses all pharmaceutically acceptable solvated forms, particularly those that exhibit an effect on the queuine-tRNA ribosyltransferase pathway, such that they are useful in the treatment of disease.

It is to be understood that, insofar as certain of the compounds of formula (I) defined herein may exist in optically active or racemic forms by virtue of one or more asymmetric carbon atoms, the invention includes within its definition any such optically active or racemic forms, particularly those that exhibit an effect on the queuine-tRNA ribosyltransferase pathway, such that they are useful in the treatment of disease.

It is to be understood that the invention relates to all tautomeric forms of the compounds of formula (I), particularly those that exhibit an effect on the queuine-tRNA ribosyltransferase pathway, such that they are useful in the treatment of disease.

It is to be understood that the invention relates to all isomeric forms of the compounds of formula (I), particularly those that exhibit an effect on the queuine-tRNA ribosyltransferase pathway, such that they are useful in the treatment of disease.

It is to be understood that the invention relates to all geometric forms of the compounds of formula (I), particularly those that exhibit an effect on the queuine-tRNA ribosyltransferase pathway, such that they are useful in the treatment of disease.

It is to be understood that the invention relates to compounds of formula (I) that are isotopically-labelled (i.e. radio-labelled). In such compounds, one or more atoms are replaced by an atom having an atomic mass or mass number different from the atomic mass or mass number typically found in nature. Examples of radionucleotides that can be included in the compounds of the invention include $^{2}H$ (also written as "D" for deuterium), $^{3}H$ (also written as "T" for tritium), $^{11}C$, $^{13}C$, $^{14}C$, $^{15}O$, $^{17}O$, $^{18}O$, $^{18}F$ and the like. The particular radionucleotide used will depend on the specific application of the radio-labelled compound.

Some compounds of the invention may contain one or more chiral centres and may therefore exist as stereoisomers. Stereoisomers may be separated using conventional techniques, such as chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example by fractional crystallisation, HPLC or flash chromatography. Alternatively, particular stereoisomers may be prepared by chiral synthesis from chiral starting materials under conditions that will not cause racemisation or epimerisation, by derivatisation with a chiral reagent or by asymmetric catalytic synthesis. When a specific stereoisomer is isolated, it is suitably isolated substantially free of other stereoisomers, for example containing less than 20%, such as less than 10%, particularly less than 5%, by weight of other stereoisomers.

It is to be understood that the compounds of formula (I) may exhibit polymorphism and the invention encompasses all such forms, particularly those that exhibit an effect on the queuine-tRNA ribosyltransferase pathway, such that they are useful in the treatment of an autoimmune disease.

A compound of formula (I), or a pharmaceutically acceptable salt or solvate thereof may be prepared by any process known to be applicable to the preparation of chemically related compounds. Such processes, when used to prepare a compound of formula (I) or a pharmaceutically acceptable salt or solvate thereof are provided as a further feature of the present invention and are illustrated by the following representative process variants in which, unless otherwise stated, X, Y, $R_1$, $R_2$, $R_3$, and x have the meanings defined hereinbefore. Necessary starting materials are commercially available or may be prepared by standard procedures of organic chemistry within the ordinary skill of an organic chemist, for example as described in conjunction with the following representative processes and within the accompanying examples.

For example, a compound of formula (I) may be prepared by a process according to Scheme 1:

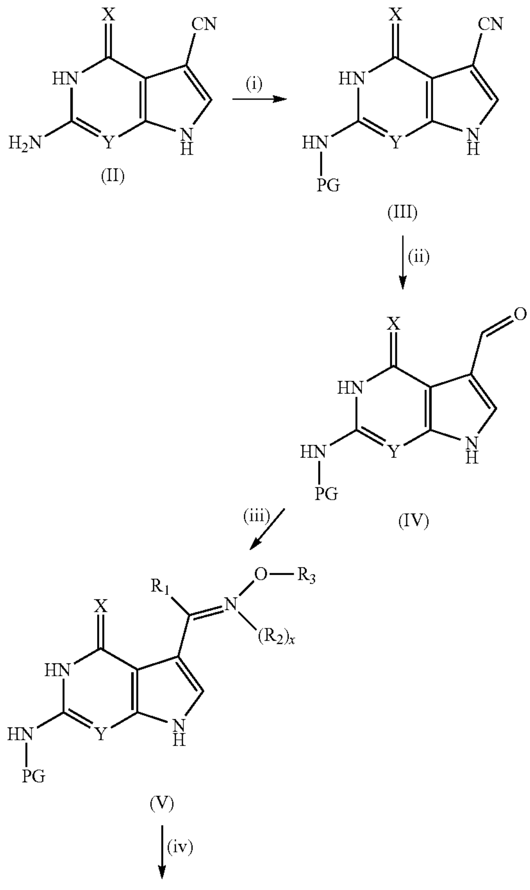

-continued

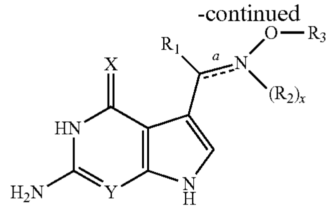

(I)

wherein PG represents a suitable amine protecting group. In Scheme 1, a compound of formula (II) is reacted with a suitable amine protecting group in step (i) to provide a compound of formula (III). In step (ii), a compound of formula (IV) is prepared from a compound of formula (III) by suitable reduction and hydrolysis steps (in either order). A suitable reducing agent for use in step (ii) when reduction preceeds hydrolysis is DiBAL. In step (iii), a compound of formula (V) is prepared by an amination of the compound of formula (IV). In step (iv), a compound of formula (I) wherein a represents a double bond is prepared by removal of the protecting group by suitable means, or a compound of formula (I) wherein a represents a single bond is prepared by conducting a reduction of the double bond using a suitable reducing agent (such as sodium cyanoborohydride), followed by removal of the protecting group by suitable means. Suitable protecting groups may be used on other substituents on the compounds of formulae (II), (III), (IV) and (V) as appropriate.

The use of protecting groups and methods of deprotection are well known to the organic chemist and a person skilled in the art would readily be able to select a suitable amine protecting group. An example of a suitable amine protecting group is triphenylmethyl (trityl). An example of a suitable hydroxyl protecting group is tert-butyl(dimethyl)silyl.

The resultant compound of the invention formed from the process described above may be isolated and purified using techniques well known in the art.

The compound of the invention may exist in a single crystal form or in a mixture of crystal forms, or may be amorphous. Thus, the compounds of the invention intended for pharmaceutical use may be administered a crystalline or amorphous products.

Medical Uses

The present invention provides a compound of the invention, or a pharmaceutically acceptable salt or solvate thereof, for use as a medicament.

The present invention also provides a compound of the invention, or a pharmaceutically acceptable salt or solvate thereof, for use in the treatment of a disease or medical condition capable of being mediated by a substrate for the queuine-tRNA ribosyltransferase pathway.

The present invention also provides the use of a compound of the invention, or a pharmaceutically acceptable salt or solvate thereof, in the manufacture of a medicament for the treatment of a disease or medical condition capable of being mediated by a substrate for the queuine-tRNA ribosyltransferase pathway.

The present invention also provides a method for treating a disease or medical condition capable of being mediated by a substrate for the queuine-tRNA ribosyltransferase pathway in a warm-blooded animal in need of such treatment, which comprises administering to said warm-blooded animal a therapeutically effective amount of a compound of the invention, or a pharmaceutically acceptable salt or solvate thereof.

The compounds of the invention are substrates for TGT (tRNA guanine transglycosylase) an enzyme complex made of two proteins known as queuine tRNA-ribosyltransferase 1, and the partner protein QTRTD1 (queuine tRNA transglycosylase domain containing 1), also referred to as QTRT2 or Qv1.

This enzyme is known to insert the natural product ‘queuine’ into $tRNA^{asp}$, $tRNA^{asn}$, $tRNA^{his}$ and $tRNA^{tyr}$ in every cell in the body. Cells which are proliferating at an abnormal rate, such as T-cells in autoimmune disease, have been found to be queuine deficient (Fergus et al., *Nutrients* 2015, 7(4):2897-2929). tRNA is essential in protein translation. Issues in protein translation are strongly associated with autoimmune diseases, inflammatory diseases and neurodegenerative diseases. Queuine mimetics that are substrate for the TGT enzyme are exclusively inserted into the same tRNAs as queuine and only at the same position on tRNA as queuine. They have been shown to act via both T-cells and the innate immune mechanisms and to normalize cytokine levels with a concomitant effect in the treatment of autoimmune diseases. Further, queuine deficiency has been shown to be associated with increased glycolysis and reduction in mitochondrial function, which in itself are markers associated with inflammation and neurodegenerative disorders (Hayes et al., Nutrients 2020 12(3)).

Without being bound by theory, it is believed that this effect on protein translation and protein folding (including the unfolded response) also has an effect in the aggregation of proteins in conditions such as Alzheimer’s disease. Additionally, it is believed that the effects on cellular metabolism and mitochondrial function can influence conditions such as Alzheimer’s disease.

The present invention provides a compound of the invention, or a pharmaceutically acceptable salt or solvate thereof, for use in the treatment of an autoimmune disease.

The present invention also provides the use of a compound of the invention, or a pharmaceutically acceptable salt or solvate thereof, in the manufacture of a medicament for the treatment of an autoimmune disease.

The present invention also provides a method for treating an autoimmune disease in a warm-blooded animal in need of such treatment, which comprises administering to said warm-blooded animal a therapeutically effective amount of a compound of the invention, or a pharmaceutically acceptable salt or solvate thereof.

The present invention provides a compound of the invention, or a pharmaceutically acceptable salt or solvate thereof, for use in the treatment of a neurodegenerative disease.

The present invention also provides the use of a compound of the invention, or a pharmaceutically acceptable salt or solvate thereof, in the manufacture of a medicament for the treatment of a neurodegenerative disease.

The present invention also provides a method for treating a neurodegenerative disease in a warm-blooded animal in need of such treatment, which comprises administering to said warm-blooded animal a therapeutically effective amount of a compound of the invention, or a pharmaceutically acceptable salt or solvate thereof.

The present invention provides a compound of the invention, or a pharmaceutically acceptable salt or solvate thereof, for use in the treatment of an inflammatory disease.

The present invention also provides the use of a compound of the invention, or a pharmaceutically acceptable salt or solvate thereof, in the manufacture of a medicament for the treatment of an inflammatory disease.

The present invention also provides a method for treating an inflammatory disease in a warm-blooded animal in need of such treatment, which comprises administering to said warm-blooded animal a therapeutically effective amount of a compound of the invention, or a pharmaceutically acceptable salt or solvate thereof.

Autoimmune diseases include:

Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG) Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease In particular, the autoimmune disease is mediated by T cells.

Preferred examples of autoimmune disease that may be treated include MS, RA, alopecia areata, optic neuritis, IBD, psoriasis and diabetes. Also included is use in transplant and co-administration with biologic drugs that suffer from immune rejection. Suitable neurodegenerative diseases include those that have an underlying autoimmune component such as dementia, Huntingdons, Alzheimer's disease, Parkinson's disease and Amyotrophic lateral sclerosis as well as depression and schizophrenia. Suitable inflammatory diseases include conditions driven by a cytokine response, or a cytokine storm.

The present invention also provides a compound of the invention, or a pharmaceutically acceptable salt or solvate thereof, for use in the treatment of MS.

The present invention also provides the use of a compound of the invention, or a pharmaceutically acceptable salt or solvate thereof, in the manufacture of a medicament for the treatment of MS.

The present invention also provides a method for treating MS in a patient in need of such treatment, which comprises administering to said patient a therapeutically effective amount of a compound of the invention, or a pharmaceutically acceptable salt or solvate thereof.

Suitable forms of MS include Relapsing Remitting (RRMS), Secondary Progressive (SPMS), Primary Progressive (PPMS) and Progressive Relapsing MS (PPMS)

The present invention also provides a compound of the invention, or a pharmaceutically acceptable salt or solvate thereof, for use in the treatment of RA.

The present invention also provides the use of a compound of the invention, or a pharmaceutically acceptable salt or solvate thereof, in the manufacture of a medicament for the treatment of RA.

The present invention also provides a method for treating RA in a warm-blooded animal in need of such treatment, which comprises administering to said warm-blooded animal a therapeutically effective amount of a compound of the invention, or a pharmaceutically acceptable salt or solvate thereof.

The compound of the invention, or a pharmaceutically acceptable salt or solvate thereof, may be administered as a sole therapy, or may be administered in combination with an additional therapeutic agent. Additional therapeutic agent(s) may be administered simultaneously, separately or sequentially with the compound of formula (I).

The present invention provides a pharmaceutical product comprising a compound of the invention, or a pharmaceutically acceptable salt or solvate thereof, and an additional therapeutic agent.

The present invention further provides a compound of the invention, or a pharmaceutically acceptable salt or solvate thereof, for use in the treatment of an autoimmune disease, where the compound of the invention, or a pharmaceutically acceptable salt or solvate thereof, is administered simultaneously, separately or sequentially with an additional therapeutic agent.

The present invention further provides a compound of the invention, or a pharmaceutically acceptable salt or solvate thereof, for use in the treatment of a neurodegenerative disease, where the compound of the invention, or a pharmaceutically acceptable salt or solvate thereof, is administered simultaneously, separately or sequentially with an additional therapeutic agent.

The present invention further provides a compound of the invention, or a pharmaceutically acceptable salt or solvate thereof, for use in the treatment of an inflammatory disease, where the compound of the invention, or a pharmaceutically acceptable salt or solvate thereof, is administered simultaneously, separately or sequentially with an additional therapeutic agent.

The invention further relates to compounds of the invention in combination with other suitable agents, for use in the treatment of MS.

The invention further relates to compounds of the invention in combination with other suitable agents, for use in the treatment of RA.

Patients suffering from MS are commonly co-administered additional therapeutic agents. For patients suffering a severe attack, intravenous corticosteroids, such as methylprednisolone or techniques such as or plasmapheresis may be coadministered with any treatment.

The effects of nerve cell damage caused by MS result in diverse forms of damage to the patient. Nerve damage can lead to pain, difficulty with control of bladder and many other issues. For this reason, additional medicaments are often prescribed to patients with MS to help treat the effects of MS damage. Suitable co-administrants would include:

For bladder problems
botulinum toxin (Botox)
desmopressin (Desmospray, Desmotabs)
oxybutynin (Ditropan, Lyrinel)
tolterodine (Detrusitol)
For depression
amitriptyline (Triptafen)
fluoxetine (Prozac)
imipramine (Tofranil)
paroxetine (Seroxat)
For erectile dysfunction
alprostadil (Caverject, MUSE, Viridal Duo)
sildenafil citrate (Viagra)
tadalafil (Cialis)
vardenafil (Levitra) For fatigue
amantadine (Lysovir, Symmetrel)
modafinil (Provigil)
For optic neuritis
steroids
For pain
amitriptyline (Triptafen)
carbamazepine (Tegretol)
gabapentin (Neurontin)
ibuprofen
imipramine (Tofranil)
lamotrigine (Lamictal)
phenytoin (Epanutim)
pregabalin (Lyrica)
For problems with walking
fampridine (Fampyra)
For psuedobulbar affect
Nuedexta
For spasticity and spasms
baclofen (Lioresal)
botulinum toxin (Botox)
carbamazepine (Tegretol)
clonazepam (Rivotril)
dantrolene (Dantrium)
diazepam (Valium)
gabapentin (Neurontin)
phenol
Tetrahydrocannabinol and cannabidiol (Sativex)
tizanidine (Zanaflex)
For tremor
clonazepam (Rivotril)
thalamotomy
For trigeminal neuralgia
carbamazepine (Tegretol)
gabapentin (Neurontin)
oxcarbazepine (Trileptal)
phenytoin (Epanutim)
pregabalin (Lyrica)

Other therapeutic agents are commonly administered to patients with MS. Other such medicaments are well known to physicians and others skilled in therapy.

Composition

The present invention provides a pharmaceutical composition comprising a compound of the invention or a pharmaceutically acceptable salt or solvate thereof, and a pharmaceutically acceptable carrier or excipient.

The composition of the invention may be in a form suitable for oral administration (such as a tablet, lozenge, hard or soft capsule, aqueous or oily suspension, emulsion, dispersible powder or granules, syrup or elixirs), for topical use (for example as a cream, ointment, gel or aqueous or oily solution or suspension), for administration by inhalation (such as a finely divided powder or a liquid aerosol), for administration in insufflation (such as a finely divided powder), or for parenteral administration (such as a sterile aqueous or oily solution for intravenous, subcutaneous, intramuscular dosing or a suppository for rectal dosing).

Suitably, the pharmaceutical composition is for oral administration, particularly in tablet form.

The compositions of the invention may be obtained by conventional procedures using conventional pharmaceutical carriers or excipients known in the art. Thus, compositions for oral use may contain, for example, one or more colouring, sweetening, flavouring and/or preservative agents.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of the invention, a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of the invention may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques.

Compounds of the invention may also be administered topically to the skin or mucosa, that is, dermally or transdermally.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. For intranasal use, the powder may comprise a bioadhesive agent, for example, chitosan or cyclodextrin The pressurised container, pump, spray, atomizer, or nebuliser contains a solution or suspension of the compound of the invention comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of the invention may also be administered directly to the eye or ear, typically in the form of drops of a micronised suspension or solution in isotonic, pH-adjusted, sterile saline.

Compounds of the invention may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148.

The amount of active ingredient (i.e. compound of formula (I) or a pharmaceutically acceptable salt or solvate thereof) that is combined with the carrier or excipient to produce a single dosage form will necessarily vary depending on the patient treated and the particular route of administration. For example, a composition intended for oral administration to humans will generally contain, for example 0.5 to 500 mg of active ingredient mixed with an appropriate and convenient amount of carrier or excipient which may vary from about 5 to about 96% by weight of the total composition.

The size of dose for therapeutic or prophylactic purposes of a compound of the invention, or a pharmaceutically acceptable salt or solvate thereof, will naturally vary according to the nature and severity of the disease, the age and sex of the patient and the route of administration, according to well-known principals of medicine. An example of a daily dosage may be, for example, 0.5 to 50 mg/kg body weight.

The compound of the invention, or a pharmaceutically acceptable salt or solvate thereof, may be administered in the form of a pro-drug, by which we mean a compound that is broken down in a warm-blooded animal such as a human to release a compound of the formula (I), or a pharmaceutically acceptable salt or solvate thereof.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18 to 25° C.;

(ii) final products had satisfactory proton and carbon nuclear magnetic resonance (NMR) spectra and/or mass spectral data;

(iii) yields are given for illustration only and are not necessarily those which can be obtained by diligent process development; preparations were repeated if more material was required;

(iv) when given, NMR data is in the form of delta values for major diagnostic protons, given in parts per million (ppm) relative to tetramethylsilane (TMS) as an internal standard, determined at 400 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(v) chemical symbols have their usual meanings; SI units and symbols are used.

2-Chloro-3-oxopropanenitrile

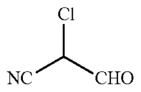

In a dry round bottomed flask under a positive pressure of argon, a suspension of NaOMe (7.14 g, 0.13 mol) in dry THF (90 mL) was cooled to −5° C. Methyl formate (9 mL, 0.15 mol) was added dropwise over 1 min by syringe and stirring was continued at −5° C. for 20 min. Then chloroacetonitrile (8.33 mL, 0.13 mol) was added dropwise via a dropping funnel over 45 min. The mixture turned from white to yellow and was stirred for a further 2 h at −5° C. at which point the reaction mixture was orange. The bath was removed and the reaction was allowed to warm up to room temperature. An aliquot of the reaction mixture was treated with a drop of concentrated HCl and analysed by TLC which indicated the presence of the desired product with an $R_f$=0.45, eluting with 100% EtOAc. The mixture was cooled to 0° C. and concentrated HCl (12 mL) was added dropwise during which time the mixture reaction became cherry-red. The resultant suspension was filtered through a pad of celite, and the celite was washed with EtOAc until the filtrate became colourless. The collected filtrates were concentrated at reduced pressure with the water bath at a temperature no higher than 40° C. to afford chloro(formyl)acetonitrile as a black oil, in quantitative yield, which was used without further purification.

2-Amino-4-oxo-4,7-dihydro-3H-pyrrolo[2,3-d]pyrimidine-5-carbonitrile

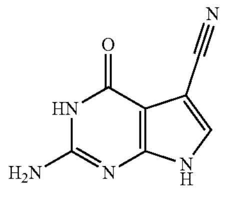 [SMILES: N#Cc1c[nH]c2nc(N)[nH]c(=O)c12]

2,4-Diamino-6-hydroxypyrimidine (3.00 g, 24 mmol) was added to a solution of sodium acetate (6.4 g, 76 mmol) in millipore water (90 mL) and stirred at 50° C. for 1 hour. While still at 50° C. a solution of crude chloro(formyl) acetonitrile (S2) (3.00 g, 32 mmol) in mQ water (44 mL) was added dropwise with a dropping funnel, during which time the reaction turned beige and heating continued for 18 h at 50° C., after which time the reaction was heated to 100° C. for 3 h. The reaction mixture was allowed to cool to room temperature and the solid removed by filtration. The solid was suspended in EtOH and 5M aqueous KOH solution was added until the solid dissolved. Charcoal was added to the solution and the mixture stirred for 30 minutes before removal of the solid by filtration. The pH of the filtrate was adjusted to pH=6 with concentrated aqueous HCl solution during which time a precipitate formed and was collected by filtration. In order to remove the final traces of water from the solid it was dissolved in a mixture of toluene/methanol 1/1 and then concentrated at reduced pressure. The resultant solid was dried over $P_2O_5$ to afford the desired compound (1.68 g, 9.6 mmol, 40% yield) as beige solid.

mp: >250° C. (decomp.).

$\delta_H$ (400 MHz, DMSO-$d_6$): 6.49 (2H, bs, $NH_2$), 7.59 (1H, s), 10.78 (1H, bs), 11.90 (1H, bs) HRMS (m/z-ES): Found: 174.0420 ($[M-H]^-$ $C_7H_4N_5O$; Requires: 174.0421)

4-Oxo-2-(tritylamino)-4,7-dihydro-3H-pyrrolo[2,3-d]pyrimidine-5-carbonitrile

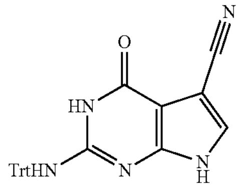

In a dry round bottomed flask under an atmosphere of argon, trityl chloride (1.20 g, 4.28 mmol) was added to a solution of 2-amino-4,7-dihydro-4-oxo-3H-pyrrolo[2,3-d] pyrimidine-5-carbonitrile (0.50 g, 2.85 mmol) in dry pyridine (29 mL). The mixture reaction was heated at 90° C. for 48 h. The reaction mixture was concentrated under reduced pressure then absorbed on silica gel and purified by flash chromatography on silica gel eluting with dichloromethane/ MeOH with a gradient starting at 2% of MeOH and rising to 10%. The desired compound was obtained as a brown solid (0.63 g, 1.5 mmol, 53% yield).

mp: 196-198° C.

$\delta_H$ (400 MHz, DMSO-$d_6$): 7.13-7.26 (15H, m), 7.37 (1H, s), 7.57 (1H, bs), 10.67 (1H, bs), 11.74 (1H, bs, NH)

HRMS (m/z-ES): Found: 418.1665 ($[M+H]^+$ $C_{26}H_{26}N_5O$; Requires: 418.1662)

4-Oxo-2-(tritylamino)-4,7-dihydro-3H-pyrrolo[2,3-d]pyrimidine-5-carbaldehyde

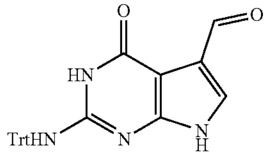

Hexamethyldisilazane (HMDS) (6 mmol, 1.3 mL) was added to a mixture of 4,7-dihydro-4-oxo-2-[(triphenylmethyl)amino]-3H-pyrrolo[2,3-d]pyrimidine-5-carbonitrile (1.30 g, 3 mmol) with ammonium sulphate (397 mg, 0.3 mmol) in dry toluene (8 mL) in a round bottomed flask. A reflux condenser was fitted, and the flask was heated at reflux temperature overnight. The mixture was cooled to room temperature and concentrated under reduced pressure. Under a positive pressure of argon, the crude reaction mixture was solubilised in dry dichloromethane (8 mL) and cooled to −78° C. At this temperature, diisobutylaluminium hydride (DiBAL-H) (4.5 mL, 1 M in dichloromethane, 4.5 mmol) was added dropwise. After 2 hours, analysis by thin layer chromatography (TLC) (ethyl acetate (EtOAc) 100%) indicated that some starting material remained. So, a further 2 mL diisobutylaluminium hydride (DiBAL-H) solution was added dropwise. After 1 hour, the reaction was complete and a mixture of water/acetic acid (9/1, 3.5 mL) was added at −78° C. The reaction mixture was allowed to warm to room temperature slowly. A mixture of ethyl acetate/water (1/1, 300 mL) was added to the reaction mixture and stirring continued at room temperature for 2 hours. The layers were separated and the organic layer was washed with brine and the aqueous layers were extracted with ethyl acetate. The combined organic fractions were dried over anhydrous magnesium sulfate, filtered and concentrated at reduced pressure. The crude reaction product was filtered through a pad of silica gel eluting with ethyl acetate to afford a yellow solid (1.01 g, 2.38 mmol, 76%).

mp: >250° C. (decomp.).

$\delta_H$ (400 MHz, DMSO-$d_6$): 7.15-7.29 (16H, m), 7.54 (1H, bs, NH), 9.99 (1H, s), 10.64 (1H, bs), 11.81 (1H, bs, NH)

HRMS (m/z-ES): Found: 443.1478 ($[M+Na]^+$ $C_{26}H_{20}N_4NaO_2$; Requires: 443.1478)

4-oxo-2-(tritylamino)-4,7-dihydro-3H-pyrrolo[2,3-d] pyrimidine-5-carbaldehyde O-phenethyl oxime

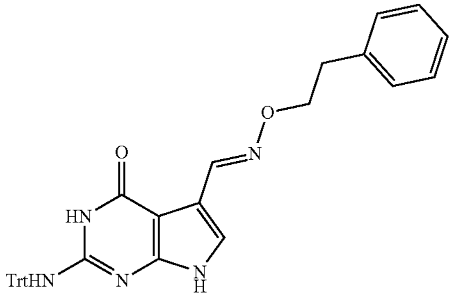

A solution of 4-Oxo-2-(tritylamino)-4,7-dihydro-3H-pyrrolo[2,3-d]pyrimidine-5-carbaldehyde (300 mg, 0.72 mmol) and O-(2-phenylethyl)hydroxylamine (107 mg, 0.78 mmol) in MeOH (5 $cm^3$) was prepared. A spatula tip of $Na_2SO_4$ was added and the resulting suspension was stirred at room temperature for 20 h before being concentrated in vacuo and purified by flash chromatography (7:3 Hex/EtOAc) to yield 4-oxo-2-(tritylamino)-4,7-dihydro-3H-pyrrolo[2,3-d]pyrimidine-5-carbaldehyde O-phenethyl oxime as a white powder (150 mg, 39%), mp: 188-191° C.

$\delta_H$ (400 MHz, DMSO-$d_6$): 2.89 (2H, t, J 6.9), 4.16 (2H, t, J 6.9), 6.83 (1H, s), 7.17-7.29 (20H, m), 7.44 (1H, s), 8.29 (1H, s), 10.45 (1H, bs), 11.24 (1H, bs)

$\delta_C$ (100 MHz, DMSO-$d_6$): 35.3, 35.4, 70.5, 74.0, 99.1, 110.4, 115.4, 126.5, 127.0, 128.1, 128.7, 129.3, 139.1, 143.7, 145.3, 150.3, 159.0

HRMS (m/z-APCI): Found: 540.2393 ($[M+H]^+$ $C_{34}H_{30}N_5O_2$; Requires: 540.2394)

$v_{max}$ (film)/$cm^{-1}$: 1630, 1676, 2105, 2927, 3398, 3676

Example 1 2-Amino-5-((phenethoxyamino)methyl)-3,7-dihydro-4H-pyrrolo[2,3-d]pyrimidin-4-one

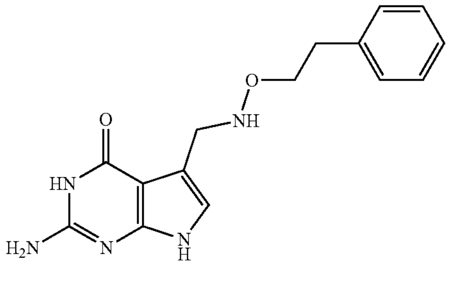 [SMILES: Nc1nc2[nH]cc(CNOCCc3ccccc3)c2c(=O)[nH]1]

To a solution of 4-oxo-2-(tritylamino)-4,7-dihydro-3H-pyrrolo[2,3-d]pyrimidine-5-carbaldehyde O-phenethyl oxime (130 mg, 0.25 mmol) in $CH_2Cl_2$ (5 $cm^3$) was added $NaCNBH_3$ (32 mg, 0.51 mmol). Methanolic HCl (1.25 M) was added dropwise to adjust the pH to approximately 3. The resulting solution was stirred at room temperature for 3 h, with care taken to ensure the pH was maintained at 3. Additional methanolic HCl was added when necessary. The reaction mixture was then diluted with $H_2O$ (15 $cm^3$) and extracted with $CH_2Cl_2$ (3×10 $cm^3$). The combined organic extracts were dried ($MgSO_4$) and concentrated in vacuo before being taken up into 1 M HCl in dioxane and stirred at room temperature for 1 h. The precipitate of product was isolated by vacuum filtration and washed with $Et_2O$ to yield the HCl salt of 2-Amino-5-((phenethoxyamino)methyl)-3,7-dihydro-4H-pyrrolo[2,3-d]pyrimidin-4-one as a white powder (35 mg, 50%), 250° C. (decomp.).

$\delta_H$ (400 MHz, DMSO-$d_6$): 2.90 (2H, t, J 6.6), 4.28 (2H, t, J 6.6), 4.43 (2H, s), 6.44 (2H, bs), 6.79 (1H, d, J 2.2), 7.17-7.27 (5H, m), 10.97 (1H, bs), 11.30 (1H, bs)

$\delta_C$ (100 MHz, DMSO-$d_6$): 35.4, 35.6, 66.8, 98.9, 111.4, 117.2, 125.2, 128.2, 129.2, 129.9, 148.3, 125.7, 160.0

HRMS (m/z-APCI): Found: 300.1462 ($[M+H]^+$ $C_{15}H_{18}N_5O_2$; Requires: 300.1455)

$v_{max}$ (film)/$cm^{-1}$: 1670, 2531, 3024, 3261

4-oxo-2-(tritylamino)-4,7-dihydro-3H-pyrrolo[2,3-d] pyrimidine-5-carbaldehyde O-methyl oxime

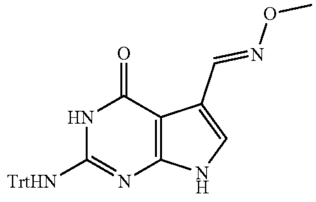

4-oxo-2-(tritylamino)-4,7-dihydro-3H-pyrrolo[2,3-d]pyrimidine-5-carbaldehyde O-methyl oxime was prepared using the same procedure as for 4-oxo-2-(tritylamino)-4,7-dihydro-3H-pyrrolo[2,3-d]pyrimidine-5-carbaldehyde O-phenethyl oxime above, except using methoxylamine hydrochloride (94.0 mg, 0.78 mmol) and triethylamine (156 μL, 0.78 $cm^3$) in place of O-(2-phenylethyl)hydroxylamine. The crude reaction product was purified by flash chromatography (7:3 Hex/EtOAc) to yield 4-oxo-2-(tritylamino)-4,7-dihydro-3H-pyrrolo[2,3-d]pyrimidine-5-carbaldehyde O-methyl oxime as a white powder (137 mg, 42%), as a single isomer, mp: 186-190° C.

$\delta_H$ (400 MHz, DMSO-$d_6$): 3.74 (3H, s), 6.81 (1H, d, J 2.3), 7.17-7.21 (4H, m), 7.22-7.29 (1H, m), 7.45 (1H, s), 8.29 (1H, s), 10.44 (1H, bs), 11.26 (1H, bs)

$\delta_C$ (100 MHz, DMSO-$d_6$): 61.4, 70.5, 99.1, 110.3, 115.3, 127.0, 128.1, 129.1, 143.6, 145.3, 150.3, 150.5, 159.0

$v_{max}$ (film)/$cm^{-1}$: 1066, 1250, 1552, 1611, 1654, 3663

Example 2 2-Amino-4-oxo-4,7-dihydro-3H-pyrrolo [2,3-d]pyrimidine-5-carbaldehyde O-methyl oxime

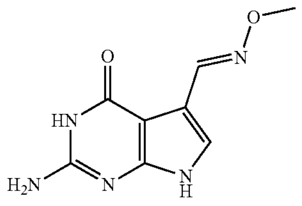

The compound 4-oxo-2-(tritylamino)-4,7-dihydro-3H-pyrrolo[2,3-d]pyrimidine-5-carbaldehyde O-methyl oxime was dissolved in 1 M HCl in dioxane (9 eq.) and the solution stirred at room temperature overnight during which time a precipitate of the product formed. The product was isolated via vacuum filtration and washed with $CH_2Cl_2$ to yield the HCl salt of 2-Amino-4-oxo-4,7-dihydro-3H-pyrrolo[2,3-d]

pyrimidine-5-carbaldehyde O-methyl oxime as a white powder (10 mg, 16%) containing an inseparable mixture of E/Z isomers in a 97:3 ratio, mp: >250° C. (decomp.).

$\delta_H$ (400 MHz, DMSO-$d_6$): 3.87 (1H, s), 6.18 (2H, bs), 7.38 (1H, s), 7.84 (1H, s), 10.46 (1H, bs), 11.47 (1H, bs)

$\delta_C$ (100 MHz, DMSO-$d_6$): 41.0, 97.8, 109.0, 123.0, 139.4, 150.6, 153.4, 159.5

$\nu_{max}$ (film)/cm$^{-1}$: 1053, 1593, 1672, 2854, 3132

4-oxo-2-(tritylamino)-4,7-dihydro-3H-pyrrolo[2,3-d] pyrimidine-5-carbaldehyde O-benzyl oxime

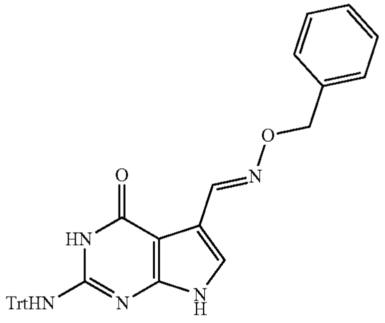

4-oxo-2-(tritylamino)-4,7-dihydro-3H-pyrrolo[2,3-d]pyrimidine-5-carbaldehyde O-benzyl oxime was prepared using the same procedure as for 4-oxo-2-(tritylamino)-4,7-dihydro-3H-pyrrolo[2,3-d]pyrimidine-5-carbaldehyde O-phenethyl oxime above, except using O-benzylhydroxylamine in place of O-(2-phenylethyl)hydroxylamine and the product purified by flash chromatography (7:3 Hex/EtOAc) to yield 4-oxo-2-(tritylamino)-4,7-dihydro-3H-pyrrolo[2,3-d]pyrimidine-5-carbaldehyde O-benzyl oxime as a white powder (120 mg, 32%) as a 9:1 mixture of E/Z isomers, mp: 186-189° C.

$\delta_H$ (400 MHz, DMSO-$d_6$): major isomer—5.02 (2H, bs), 6.81 (1H, d, J 1.7), 7.17-7.35 (20H, m), 7.45 (1H, s), 8.36 (1H, s), 10.44 (1H, bs), 11.27 (1H, bs) minor isomer—5.13 (s), 7.17-7.35 (m), 7.48 (s), 7.84 (s), 10.51 (bs), 11.37 (bs)

$\delta_C$ (100 MHz, DMSO-$d_6$): major isomer—70.5, 75.3, 99.1, 110.3, 115.5, 127.0, 127.1, 128.0, 128.1, 128.5, 128.7, 129.1, 138.4, 144.1, 145.3, 150.3, 150.5, 159.0 minor isomer—70.6, 75.8, 98.5, 109.0, 127.0, 128.0, 128.7, 128.9, 138.7, 140.0, 145.3, 149.7, 150.8, 159.2 (not all peaks visible due to overlapping the aromatic region)

HRMS (m/z-APCI): Found: 526.2232 ([M+H]$^+$ $C_{33}H_{28}N_5O_2$; Requires: 526.2237)

$\nu_{max}$ (film)/cm$^{-1}$: 1656, 2230, 2902, 2973, 3662

Example 3 2-Amino-5-(((benzyloxy)amino)methyl)-3,7-dihydro-4H-pyrrolo[2,3-d]pyrimidin-4-one

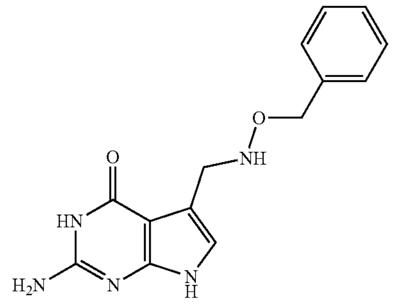 [SMILES: Nc1nc2[nH]cc(CNOCc3ccccc3)c2c(=O)[nH]1]

To a solution of 4-oxo-2-(tritylamino)-4,7-dihydro-3H-pyrrolo[2,3-d]pyrimidine-5-carbaldehyde O-benzyl oxime (50 mg, 0.18 mmol) in $CH_2Cl_2$ (5 cm$^3$) was added $NaCNBH_3$ (23 mg, 0.36 mmol). Methanolic HCl (1.25 M) was added dropwise to adjust the pH to approximately 3. The resulting solution was stirred at room temperature for 3 h, with care taken to ensure the pH was maintained at 3. Additional methanolic HCl was added when necessary. The reaction mixture was then diluted with $H_2O$ (15 cm$^3$) and extracted with $CH_2Cl_2$ (3x10 cm$^3$). The combined organic extracts were dried ($MgSO_4$) and concentrated in vacuo before being taken up into 1 M methanolic HCl and stirred at room temperature for 1 h. The precipitate of product was isolated by vacuum filtration and washed with $Et_2O$ to yield the HCl salt of 2-Amino-5-(((benzyloxy)amino)methyl)-3,7-dihydro-4H-pyrrolo[2,3-d]pyrimidin-4-one as a white powder (11 mg, 12%), mp: >250° C. (decomp.).

$\delta_H$ (400 MHz, DMSO-$d_6$): 4.32 (2H, s), 5.01 (2H, s), 6.34 (2H, bs), 6.79 (1H, s), 7.35-7.36 (5H, m), 10.86 (1H, bs), 11.24 (1H, bs)

$\delta_C$ (100 MHz, DMSO-$d_6$): 44.6, 75.1, 99.0, 107.1, 128.4, 129.0, 129.7, 130.3, 134.0, 146.5, 152.6, 159.4

HRMS (m/z-APCI): Found: 286.1299 ([M+H]$^+$ $C_{14}H_{16}N_5O_2$; Requires: 286.1292)

$\nu_{max}$ (film)/cm$^{-1}$: 1604, 1672, 2764, 2971

Example 4 2-Amino-4-oxo-4,7-dihydro-3H-pyrrolo [2,3-d]pyrimidine-5-carbaldehyde oxime

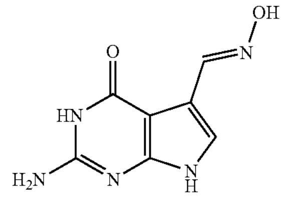 [SMILES: Nc1nc2[nH]cc(/C=N/O)c2c(=O)[nH]1]

2-Amino-4-oxo-4,7-dihydro-3H-pyrrolo[2,3-d]pyrimidine-5-carbaldehyde oxime was prepared from 4-Oxo-2-(tritylamino)-4,7-dihydro-3H-pyrrolo[2,3-d]pyrimidine-5-carbaldehyde using the same procedure as for 2-Amino-4-oxo-4,7-dihydro-3H-pyrrolo[2,3-d]pyrimidine-5-carbaldehyde O-phenethyl oxime above, except using hydroxylamine hydrochloride and triethylamine in place of O-(2-phenylethyl)hydroxylamine. The compound 4-oxo-2-(tritylamino)-4,7-dihydro-3H-pyrrolo[2,3-d]pyrimidine-5- carbaldehyde oxime was deprotected using the same general procedure described in Example 1 above, except using 1M HCl in dioxane, to yield the HCl salt of 2-Amino-4-oxo-4,7-dihydro-3H-pyrrolo[2,3-d]pyrimidine-5-carbaldehyde oxime as a white powder (34 mg, 39%) containing an inseparable mixture of E/Z isomers in a 92:8 ratio, mp>250° C. (decomp.).

$\delta_H$ (400 MHz, DMSO-$d_6$): major isomer—7.54 (1H, d, J 2.4), 7.84 (1H, s), 11.00 (1H, bs), 11.67 (1H, bs) minor isomer—7.16 (d, J 2.2), 8.37 (s), 11.81 (bs)

$\delta_C$ (100 MHz, DMSO-$d_6$): major isomer—102.7, 114.6, 129.2, 142.9, 143.0, 156.9, 162.7 minor isomer—102.5, 115.9, 127.9, 146.2, 146.3, 157.6, 163.5

HRMS (m/z-APCI): Found: 192.0525 ($[M-H]^-$ $C_7H_6N_5O_2$; Requires: 192.0527)

$v_{max}$ (film)/$cm^{-1}$: 1578, 1671, 2625, 2971, 3088, 3676

As an alternative procedure 2-Amino-4-oxo-4,7-dihydro-3H-pyrrolo[2,3-d]pyrimidine-5-carbaldehyde oxime was prepared by treating 4-Oxo-2-(tritylamino)-4,7-dihydro-3H-pyrrolo[2,3-d]pyrimidine-5-carbaldehyde (150 mg) with O-(tert-Butyldimethylsilyl) hydroxylamine (60 mg) and a trace of anhydrous sodium sulfate in methanol (3 mL). After stirring for 95 mins the volatiles were removed and the crude reaction mixture dissolved in ethyl acetate before being washed with 10% aqueous sodium hydrogen carbonate. The combined organic fractions were dried with anhydrous magnesium sulfate before removal of the volatiles at reduced pressure. Purification was performed by column chromatography on silica gel eluting with 30% ethyl acetate in hexane giving the expected oxime (120 mg). Deprotection was achieved by treating a cooled (0° C.) solution of the protected oxime (100 mg) in 1,4-dioxane (1.5 mL) and methanol (0.5 mL) with 4M HCl in dioxane (0.5 mL). After five minutes the cooling bath was removed and the reaction mixture stirred for a further ninety minutes. The resultant precipitate was removed by filtration and washed with ether three times to yield the HCl salt of 2-Amino-4-oxo-4,7-dihydro-3H-pyrrolo[2,3-d]pyrimidine-5-carbaldehyde oxime as a white powder (35 mg) containing an inseparable mixture of E/Z isomers in a 99:1 ratio in favour of the major isomer described above.

$\delta_H$ (400 MHz, DMSO-$d_6$): major isomer—7.54 (1H, d, J 2.4), 7.84 (1H, s), 11.00 (1H, bs), 11.67 (1H, bs)

The compounds of the Examples were tested in the following biological assays:

The example compounds were tested to confirm they are substrate for the queuine-tRNA ribosyltransferase enzyme complex.

Compounds capable of acting as a queuine-tRNA ribosyltransferase enzyme complex substrate may be identified by use of a displacement assay as described below:

Production of [8-$^{14}$C] Guanine Labeled tRNA (tRNA*)

Components were added in the order listed in Table 1. Before adding the 8-[$^{14}$C] guanine solution to the reaction the solution was neutralised with an equal volume (vol/vol) 0.01 M NaOH, as the [8-$^{14}$C] Guanine is supplied in 0.01 M HCl aqueous solution. In vitro synthesised human tyrosyl tRNA was prepared by T7 transcription in ultrapure nuclease-free water as described previously (Alqasem et al., 2020). Recombinant human QTRT1 enzyme containing an N-terminal polyhistidine tag and human QTRT2 containing a C-terminal TEV-Strep-Tag®II tag were produced in BL21 (DE3) tgt::$Km_r$ cells as described previously (Alqasem et al., 2020).

TABLE 1

Components of [8-$^{14}$C] Guanine tRNA labeling reaction

| Component | Volume (μL) | Final conc. |
|---|---|---|
| 1M Tris-HCl pH 7.5 | 7.5 | 50 mM |
| 5M NaCl | 0.6 | 20 mM |
| 1M $MgCl_2$ | 0.75 | 5 mM |
| 1M DTT | 0.3 | 2 mM |
| Human $tRNA^{Tyr}$ | 30 | 10 μM |
| RNase free $H_2O$ | Up to 469 μL | |
| QTRT:QTRT2 | 21 | 700 nM |
| [8-$^{14}$C] guanine | 10 | 200 nM |

The reaction was incubated for 1 hour at 37° C. The reaction mixture was extracted by the addition of an equal volume (500 μL) of Acid Phenol:chloroform (5:1; pH 4.5) and centrifuged at 16,000×g for 5 min. The upper aqueous phase was transferred to a new 1.5 mL tube. The radiolabelled tRNA with [8-$^{14}$C] guanine in the third position of the anticodon loop (tRNA*) was precipitated by the addition of 0.1 volume (50 μL) of 3 M sodium acetate (aq.) and 2 volumes of ethanol (1 mL) and incubated overnight at −20° C. The next morning, the tRNA* was pelleted by centrifugation at 16,000×g for 20 min at 4° C. The pellet was washed with 1 mL of ice-cold 70% ethanol, without disturbing the pellet. The tRNA* pellet was resuspended in 30 μL nuclease-free water and the concentration measured spectrophotometrically at $A_{260}$.

Displacement Assays

Each reaction was set up in triplicate and incubated for 30 mins at 37° C. Each of the components in the reaction were added in the order shown in Table 2, with the tRNA* added last to initiate the reaction. 'Compound' refers to the compounds of the invention that are under investigation.

TABLE 2

Components of [8-$^{14}$C] guanine displacement assays

| Component | Volume (μL) | Final Concentration |
|---|---|---|
| 1M Tris-HCl pH 7.5 | 7.5 | 50 mM |
| 5M NaCl | 0.6 | 20 mM |
| 1M $MgCl_2$ | 0.75 | 5 mM |
| 1M Dithiothreitol | 0.3 | 2 mM |
| Compound (10 mM stock) | 0.5 | 50 μM |
| hQTRT1:hQTRT2 | 8.0 | 100 nM |
| RNase free $H_2O$ | up to 90 | — |
| tRNA* (1 μM stock) | 10 | 10 μM |

After 30 mins the reactions were quenched by mixing with 2.5 ml ice-cold 10% trichloroacetic acid (TCA) and placed on ice for one hour to precipitate the tRNA. The RNA precipitate was collected using vacuum filtration onto a GF/C 2.4-cm glass fiber filter disks (set up in a Millipore Polymeric Vacuum Filter manifold). Each disk was rinsed with 40 ml ice-cold 5% TCA. The filters were vacuum dried by rinsing them with 5 ml of freshly-made, ice-cold 95% ethanol. The vacuum manifold was disassembled, the filters recovered and dried again at room temperature before being placed in scintillation vials containing 10 ml of Ecoscint A and radioactivity levels measured by scintillation counting.

In this assay, maximum displacement by 50 μM queuine base, the natural substrate of the queuine-tRNA ribosyltransferase enzyme complex, is >98% of the [$^{14}$C] guanine. Background displacement values were ≤2%. Therefore, a displacement of ≥5% is considered a positive substrate for TGT.

All compounds of the present invention were shown to have a displacement of ≥5% and thus shown to be substrate for the TGT enzyme complex.

To demonstrate the efficacy of the compounds of the present invention in treating disease, the compounds were assayed in a variety of disease models and testing on samples from human patients.

Synovial Fibroblast Assay

To assess the compounds in human rheumatoid arthritis samples the following protocol was employed:

Isolation of Primary Fibroblasts: RA synovial biopsies were digested with 1 mg/ml collagenase type 1 (Worthington Biochemical, Freehold, NJ, USA) in RPMI-1640 (Gibco-BRL, Paisley, UK) for 4 hr at 37° C. in humidified air with 5% $CO_2$. Dissociated cells were grown to confluence in RPMI 1640, 10% FCS (Gibco-BRL), 10 ml of 1 mmol/l HEPES (Gibco-BRL), penicillin (100 units/ml; Bioscience), streptomycin (100 units/ml; Bioscience) and fungizone (0.25 μg/ml; Bioscience) before passaging. Cells were used between passages 3-8.

Compounds (200 μm) were tested on n=3 RASFCs

RASFCs were grown to 80% confluency in 48 well plates. RASFCs were treated with TNF (10 ng/ml) in the presence of 200 μm of each compound. Media was replaced after 24 h and fresh media and compound was added. Cell supernatants were collected at 72 hr time point. DMSO treated cells were used as a vehicle control (Red dotted line represents DMSO control).

IL-6 ELISA: Levels of pro-inflammatory cytokine IL6 were measured in cultured RASFC supernatants by specific ELISA (R&D systems, UK) according to manufacturer's conditions.

This assay measures the production of IL-6 as an indication of immune system activation: the lower the value the better from the point of view of alleviating RA symptoms. All compounds of the invention showed an effect compared to the DMSO vehicle that represents no treatment. Additionally, the compounds of the invention showed comparable or better activity than the JAK-STAT inhibitor Tofacitinib (Xeljanz, Pfizer). Results for specific example compounds are provided below.

| Example No. | Structure | Level of IL6 expression compared to vehicle |
|---|---|---|
| Vehicle | — | 100% |
| Positive control | Tofacitinib | Reduction to 58% |
| Example 1 | 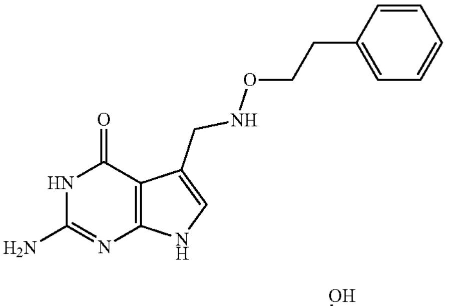 | Reduction to 17% |
| Example 4 | 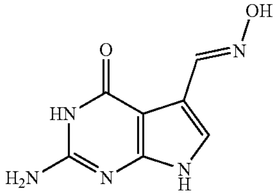 [SMILES: Nc1nc2[nH]cc(/C=N/O)c2c(=O)[nH]1] | Reduction to 15% |
| Example 2 | 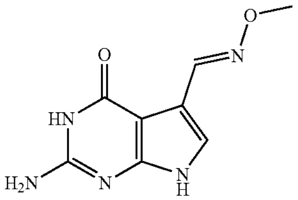 | Reduction to 15% |

Experimental Autoimmune Encephalomyelitis (EAE)

To demonstrate the efficacy of these compounds in multiple sclerosis the molecules were tested in the gold standard 'EAE' model of MS. To assess the potential of these compounds in vivo, a chronic monophasic EAE disease in mice was induced before treatment with the new chemical entity (NCE). EAE Disease was induced in 8-10 week old female mice (C57BL/6) by sub-cutaneous (s.c.) injection of 200 μl emulsion containing 100 μg $MOG_{33-55}$ peptide (Genscript) in 50% Complete Freund's Adjuvant (CFA; 50% CFA containing 4 mg/ml heat-inactivated Mycobacterium tuberculosis and 50% incomplete Freund's adjuvant (Chondrex)). On the same day, mice were administered 200 ng Pertussis Toxin (Kaketsuken, Japan) intraperitoneally (i.p.) and again two days later.

Disease severity was recorded every 24 hours and scores were attributed as follows: 0-Normal; 1-flaccid tail; 2-imparied/wobbly gait; 3-complete hind limb weakness; 4-hind limb and forelimb paralysis; 5-moribund state/dead. Protocol is based on the Nature Protocols for Active induction of experimental allergic encephalomyelitis, which includes the scoring methodology: Stromnes I M, Goverman J M (2006) Active induction of experimental allergic encephalomyelitis. Nat Protoc. 1(4):1810-9.

Upon reaching a clinical score of between 1.5 and 2 animals were either administered 200 μl of PBS as control or a 200 μL volume of queuine-mimetic compound of the examples at a concentration of 4 mM concentration intraperitoneally (i.p.) each day for a total of 7 days.

As expected, control animals displayed a consistent worsening of disease over the course of the experiment. By contrast, diseased animals treated with the compounds of the examples showed a brief elevation in disease severity followed by a gradual recovery.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. A compound of formula (I):

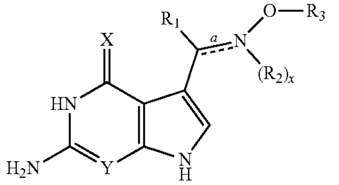

(I)

or pharmaceutically acceptable salt or solvate thereof, wherein:

Y is selected from C or N;

X is O;

bond a is a single or double bond;

x is 1 when a is a single bond and x is 0 when a is a double bond;

$R_1$ is selected from hydrogen and methyl;

$R_2$ (when present) is selected from hydrogen and methyl;

$R_3$ is selected from hydrogen, (1-6C)alkyl and (1-6C)alkyl-phenyl, wherein said phenyl is optionally substituted by one or more substituents each independently selected from hydroxy, (1-6C)alkoxy, (1-6C)alkyl and halo.

2. A compound of formula (I) according to claim 1, or pharmaceutically acceptable salt or solvate thereof, wherein Y is N.

3. A compound of formula (I) according to claim 1, or pharmaceutically acceptable salt or solvate thereof, wherein $R_1$ is hydrogen.

4. A compound of formula (I) according to claim 1, or pharmaceutically acceptable salt or solvate thereof, wherein a is a double bond and x is 0.

5. A compound of formula (I) according to claim 1, or pharmaceutically acceptable salt or solvate thereof, wherein a is a single bond and x is 1.

6. A compound of formula (I) according to claim 5, or pharmaceutically acceptable salt or solvate thereof, wherein $R_2$ is hydrogen.

7. A compound of formula (I) according to claim 1, or pharmaceutically acceptable salt or solvate thereof, wherein $R_3$ is selected from hydrogen, (1-3C)alkyl, and (1-4C)alkyl-phenyl, wherein said phenyl is optionally substituted by one or more substituents each independently selected from hydroxy, (1-6C)alkoxy, (1-6C)alkyl and halo.

8. A compound of formula (I) according to claim 1, or pharmaceutically acceptable salt or solvate thereof, wherein $R_3$ is selected from hydrogen, methyl and (1-2C)alkyl-phenyl, wherein said phenyl is optionally substituted by one or more substituents each independently selected from hydroxy, (1-6C)alkoxy, (1-6C)alkyl and halo.

9. A compound of formula (I) according to claim 1, or pharmaceutically acceptable salt or solvate thereof, selected from:

2-amino-5-((phenethoxyamino)methyl)-3,7-dihydro-4H-pyrrolo[2,3-d]pyrimidin-4-one;

2-amino-4-oxo-4,7-dihydro-3H-pyrrolo[2,3-d]pyrimidine-5-carbaldehyde O-methyl oxime;

2-amino-5-(((benzyloxy)amino)methyl)-3,7-dihydro-4H-pyrrolo[2,3-d]pyrimidin-4-one; and 2-amino-4-oxo-4,7-dihydro-3H-pyrrolo[2,3-d]pyrimidine-5-carbaldehyde oxime.

10. A medicament comprising the compound of formula (I) according to claim 1, or pharmaceutically acceptable salt or solvate thereof.

11. A method of treating a patient suffering from a disease or medical condition capable of being mediated by a substrate for the queuine-tRNA ribosyltransferase pathway, the method comprising:

administering to the patient a compound of formula (I) according to claim 1, or pharmaceutically acceptable salt or solvate thereof.

12. The method of claim 11, wherein the disease is an autoimmune disease.

13. The method of claim 11, wherein the disease is selected from a group consisting of: multiple sclerosis and rheumatoid arthritis.

14. The method of claim 11, wherein the disease or medical condition is selected from a group consisting of: a neurodegenerative disease, a neurodegenerative condition, an inflammatory disease, and an inflammatory condition.

15. A pharmaceutical composition comprising a compound of formula (I) according to claim 1, or pharmaceutically acceptable salt or solvate thereof, and a pharmaceutically acceptable carrier or excipient.

16. A pharmaceutical product comprising a compound of formula (I) according to claim 1, or pharmaceutically acceptable salt or solvate thereof, and an additional therapeutic agent.

17. A pharmaceutical product according to claim 16, wherein the additional therapeutic agent comprises a medicament for the treatment of an autoimmune disease.

* * * * *